(12) United States Patent
Griffiths et al.

(10) Patent No.: US 7,678,073 B2
(45) Date of Patent: Mar. 16, 2010

(54) VORTEX FEATURE FOR DRUG DELIVERY SYSTEM

(75) Inventors: Steven M. Griffiths, Ellicott City, MD (US); Robert L. Hill, Abingdon, MD (US); Matthew P. Robben, Pittsford, NY (US)

(73) Assignee: Meridian Medical Technologies, Inc., Columbia, MD (US)

( * ) Notice: Subject to any disclaimer, the term of this patent is extended or adjusted under 35 U.S.C. 154(b) by 247 days.

(21) Appl. No.: 11/846,601

(22) Filed: Aug. 29, 2007

(65) Prior Publication Data

US 2008/0077083 A1 Mar. 27, 2008

Related U.S. Application Data

(60) Provisional application No. 60/841,709, filed on Aug. 31, 2006.

(51) Int. Cl.
*A61M 37/00* (2006.01)
(52) U.S. Cl. ....................................................... 604/85
(58) Field of Classification Search ................... 604/85, 604/89–91, 518, 82, 92
See application file for complete search history.

(56) References Cited

U.S. PATENT DOCUMENTS

| | | | | |
|---|---|---|---|---|
| 2,591,046 A | * | 4/1952 | Brown | 604/90 |
| 2,668,084 A | * | 2/1954 | Saxton | 239/491 |
| 3,164,303 A | * | 1/1965 | Trautmann | 222/190 |
| 3,712,301 A | * | 1/1973 | Sarnoff | 604/136 |
| D268,112 S | * | 3/1983 | Sugiura | D15/7 |
| 4,599,082 A | | 7/1986 | Grimard | |
| 4,971,254 A | * | 11/1990 | Daly et al. | 239/489 |
| 5,125,892 A | * | 6/1992 | Drudik | 604/90 |
| 5,207,384 A | * | 5/1993 | Horsting | 239/463 |
| 5,336,180 A | * | 8/1994 | Kriesel et al. | 604/82 |
| 5,354,286 A | | 10/1994 | Mesa et al. | |
| 5,489,266 A | * | 2/1996 | Grimard | 604/89 |
| 5,674,195 A | * | 10/1997 | Truthan | 604/87 |
| 5,685,846 A | | 11/1997 | Michaels, Jr. | |
| 5,725,500 A | | 3/1998 | Micheler | |
| 5,752,940 A | | 5/1998 | Grimard | |
| RE35,986 E | | 12/1998 | Ritson et al. | |
| 5,865,798 A | | 2/1999 | Grimard et al. | |
| 5,899,881 A | | 5/1999 | Grimard et al. | |
| 6,224,568 B1 | * | 5/2001 | Morimoto et al. | 604/89 |
| 6,543,448 B1 | * | 4/2003 | Smith et al. | 128/203.15 |
| 6,554,792 B2 | * | 4/2003 | Hughes | 604/85 |
| 6,641,561 B1 | | 11/2003 | Hill et al. | |
| 6,878,338 B2 | | 4/2005 | Taylor et al. | |
| 7,329,235 B2 | * | 2/2008 | Bertron et al. | 604/88 |
| 2003/0176834 A1 | * | 9/2003 | Horth et al. | 604/85 |
| 2004/0138611 A1 | * | 7/2004 | Griffiths et al. | 604/82 |
| 2005/0215954 A1 | | 9/2005 | Fago | |
| 2008/0195082 A1 | * | 8/2008 | Pauser et al. | 604/518 |

* cited by examiner

*Primary Examiner*—Nicholas D Lucchesi
*Assistant Examiner*—Diva Ranade
(74) *Attorney, Agent, or Firm*—Jones Day; Garry J. Tuma (57) ABSTRACT

An automatic injector separately stores liquid and dry components in respective compartments. When the injector is activated, a fluid-directing member between the liquid and dry compartments causes the liquid component to form a vortex as the liquid flows into the dry compartment. This allows the two components to combine more thoroughly and quickly to form a liquid solution that is delivered to an injection site.

35 Claims, 10 Drawing Sheets

VORTEX FEATURE FOR DRUG DELIVERY SYSTEM

CROSS REFERENCE TO RELATED APPLICATION

This claims the benefit of U.S. Provisional Application No. 60/841,709, filed Aug. 31, 2006, the entire contents of which are incorporated herein by reference thereto.

FIELD OF THE INVENTION

The invention relates to drug delivery devices that deliver therapeutic agents. More particularly, the invention is directed to an automatic injector that quickly combines two components to form a liquid therapeutic agent delivered to an injection site.

BACKGROUND OF THE INVENTION

An automatic injector is a device that enables intramuscular or subcutaneous administration of a therapeutic agent. An advantage of automatic injectors is that they contain a measured dose of a therapeutic agent in a sealed sterile cartridge. As such, automatic injectors can be used in emergency situations to quickly and simply inject the therapeutic agent without having to measure dosages. Another advantage of automatic injectors is that the administration of the therapeutic agent is accomplished without the user initially seeing the hypodermic needle through which the therapeutic agent is delivered, and without the user having to manually force the needle into the patient. This is particularly advantageous when the therapeutic agent is being self-administered.

In some automatic injectors, the therapeutic agent is stored as a liquid solution which is then injected. However, the long-term storage of a therapeutic agent as a liquid solution has drawbacks. For instance, some therapeutic agents are not stable in solution and thus have a shorter shelf-life than their solid counterparts. To address this concern, automatic injectors have been developed that store the therapeutic agent in solid form and mix the solid therapeutic agent with a liquid immediately prior to injection. Such devices are generally referred to as wet/dry injectors. An example of such an injector is found in U.S. Reissue Pat. No. RE 35,986, entitled "Multiple Chamber Automatic Injector," the disclosure of which is incorporated herein by reference. These injectors require the user to manually rupture a sealing member between the solid and liquid components and then manually shake the injector body to expedite dissolution of the solid component prior to injection. Unfortunately, steps such as manually shaking the injector increase the time needed to administer a dose of the therapeutic agent, which is undesirable in many emergency medical situations where rapid delivery of the therapeutic agent is needed (e.g., nerve gas and chemical agent poisoning).

Therefore, a need exists for a cost-effective automatic injector that stores a therapeutic agent in solid form, does not require manual premixing by the user, and quickly and effectively automatically mixes and delivers the therapeutic agent in a liquid solution.

SUMMARY OF THE INVENTION

The invention is directed to wet/dry automatic injectors having improved mixing capabilities. By introducing a "fluid-directing member" that causes the liquid component to form a vortex, mixing of the liquid component with the dry component is improved, including improved dissolution of the dry component into the liquid component. The vortical flow has axial, radial, and circumferential components that improve mixing. As a result, a greater amount of the dry component is dissolved in the liquid component in a shorter period of time, thus allowing the user to get a more immediate, effective dose of a therapeutic agent. Moreover, increased amounts of the dry component are ultimately delivered as compared to currently available systems.

Automatic injectors of the invention include a housing assembly having a central longitudinal axis and an interior chamber located within the housing assembly. The interior chamber has an inner side surface extending in the direction of the central longitudinal axis, a dry compartment suitable for containing a dry therapeutic agent, and a wet compartment suitable for containing a liquid component. The housing assembly also includes a seal structure positioned between the dry and wet compartments in the interior chamber. The seal structure has a sealed state that prevents liquid in the wet compartment from passing through the seal structure to the dry compartment. The seal structure also has a flow-through state that allows liquid from the wet compartment to pass there through to the dry compartment. A fluid-directing member is included at an end of the seal structure adjacent the dry compartment. The housing assembly further includes a needle assembly located therein that is in communication with the interior chamber for dispensing the liquid therapeutic agent.

The seal structure has an outer seal that sealingly engages the inner side surface of the interior chamber to prevent passage of liquid between the outer seal and the inner side surface. The outer seal has a first end adjacent the wet compartment and a second end adjacent the dry compartment. The outer seal may have an annular ridge around the second end of the outer seal. The fluid-directing member is preferably adjacent the outer seal on the second end, and is preferably integrated with the outer seal to form single unit.

In one embodiment of the invention, the seal structure has an outer seal, a rigid member in communication with the outer seal, at least one flow path, an inner seal plug, and a fluid-directing member. The outer seal attaches to the rigid member (i.e., they are configured to engage each other) and, alternatively, the outer seal and rigid member may form a single integrated unit. The fluid-directing member attaches to the rigid member and, alternatively, the fluid-directing member and the rigid member may form a single integrated unit. The rigid member may be formed from at least two rigid member parts that are welded or bonded together. The inner seal plug has a first position with respect to the rigid member that seals the liquid component in the wet compartment from the dry compartment. The inner seal plug also has a second position with respect to the rigid member that allows the liquid component to pass through the seal structure via the flow path. In one embodiment, the flow path comprises a by-pass channel that allows the liquid component to flow around the inner seal plug and through the seal structure when the inner seal plug is in the second position.

The fluid-directing member has at least one channel that has a fluid exit port with an opening into the dry compartment that fully faces the inner side surface of the chamber. In other words, the opening does not face forward (i.e., towards the needle assembly), but instead faces the side wall of the chamber. The channel is preferably helically shaped about the central longitudinal axis and is in fluid communication with the flow path of the seal structure. The channel is also preferably oriented at an angle ranging from about 80° to 90° with respect to the longitudinal axis of the housing assembly. The fluid-directing member may have a plurality of channels. For example, respective embodiments of the fluid-directing member may have one, two, three, or four helical channels. In preferred embodiments, the channels are separate; however, a fluid-directing member alternatively may have interconnected channels. Each channel preferably has at least one fluid exit port, and multiple fluid exit ports are arranged preferably equidistantly radially around the central longitudinal axis. The channels may be of shapes other than helical, provided that those shapes give the liquid component a substantial circumferential flow component and/or allow the liquid component to form a vortex within the dry compartment. For example, the channels may be circular, linear, inclined, helical, or a combination thereof. Additionally, multiple channels in the same fluid-directing member can each be of the same or similar shape or, alternatively, of different shapes. In preferred embodiments, the channels direct most if not all of the fluid into the dry compartment at angles ranging from about 80° to 90° with respect to the central longitudinal axis of the housing assembly. This facilitates formation of a vortex in the dry compartment. Optionally, the channels can be constructed to direct fluid into the dry compartment at angles ranging from about 10° to 90°.

The fluid-directing member has a preferably compact construction and is located radially inward from the outer seal on the end of the seal structure adjacent the dry compartment. The ratio of the fluid-directing member's diameter or height (measured perpendicularly to the longitudinal axis of the housing assembly) to its thickness (measured along the axis) preferably ranges from 2:1 to 1:2 and more preferably from 1.5:1 to 1:1. In some embodiments of the invention, the fluid-directing member or a portion thereof extends axially beyond the outer seal, while in others, the fluid-directing member does not extend axially beyond the outer seal. The fluid-directing member has an annular surface parallel to the central longitudinal axis, and the opening of each fluid exit port is located on the annular surface. In those embodiments where the seal structure has an annular ridge around the second end of the outer seal, certain embodiments of the fluid-directing member have the opening of at least one fluid exit port fully facing the annular ridge.

The invention is also directed to a method of assembling an automatic injector for administration of a therapeutic agent. In one embodiment, the method includes providing a chamber and inserting a seal structure in the chamber to create a wet compartment and a dry compartment. The seal structure has a sealed state and a flow-through state. The seal structure also has a helical channel adjacent the dry compartment. The helical channel is configured to allow a liquid to pass there through from the wet compartment to the dry compartment such that the liquid enters the dry compartment circumferentially at an angle of about 80° to 90° with respect to a longitudinal axis of the chamber. The method also includes loading a liquid component in the wet compartment, loading a therapeutic agent in the dry compartment, attaching a plunger to the end of the chamber adjacent the wet compartment, and attaching a needle assembly for dispensing the therapeutic agent to the other end of the chamber. The method further includes providing a housing having a hollow interior and placing the chamber, needle assembly, and plunger in the housing.

The invention is further directed to a method of preparing a liquid solution in an automatic injector, wherein the liquid solution comprises a liquid and a dry substance. In one embodiment, the method includes loading a liquid in a first compartment of a chamber and loading a dry substance in a second compartment of the chamber, the chamber having a longitudinal axis. The first and second compartments are separated from each other by a seal structure that has a sealed state and a flow-through state. The seal structure is initially in the sealed state, which seals the first compartment from the second compartment to prevent the liquid from flowing into the second compartment. The method also includes converting the seal structure from the sealed state to the flow-through state to allow the liquid to flow from the first compartment into the second compartment, and forcing the liquid to flow into the second compartment in the form of a vortex to mix with the dry substance. Note that in some embodiments, loading a dry substance occurs before loading a liquid. In other embodiments, forcing the liquid to flow into the second compartment comprises forcing the liquid to flow into the second compartment circumferentially at an angle of about 80° to 90° with respect to the longitudinal axis of the chamber. In still other embodiments, forcing the liquid to flow into the second compartment comprises forcing the liquid to flow through a helical channel into the second compartment to form a vortex in the second compartment.

BRIEF DESCRIPTION OF THE DRAWINGS

The above and other advantages of the invention will be apparent upon consideration of the following detailed description, taken in conjunction with the accompanying drawings, in which like reference characters refer to like parts throughout, and in which.

DETAILED DESCRIPTION OF THE INVENTION

The invention is directed to wet/dry automatic injectors that have improved mixing capabilities. The automatic injectors of the invention include a fluid-directing member that has at least one, preferably helical, channel. As liquid passes through and out of the helical channel of the fluid-directing member, a vortex is created. As used herein, a "vortex" may be any one or all of the following: a mass of fluid with a whirling or circular motion that tends to form a cavity or vacuum in the center, fluid flow that resembles a whirlpool or eddy, and/or fluid flow that has an angular velocity and a substantial circumferential flow component. As used herein, "substantial" means more than half. A vortex of liquid injection solution improves and accelerates the mixing and dissolution of the dry therapeutic agent.

Note that the invention is not limited to any one type of automatic injector device. For example, the invention may include a nose-activated auto-injector, as described for example in U.S. Pat. No. 5,354,286, the disclosure of which is incorporated herein by reference. The invention may also include a push-button type auto-injector, wherein the user removes an end cap assembly and presses a button to trigger the injection process, as described for example in U.S. Pat. No. 6,641,561. Furthermore, the features described and illustrated herein can be used singularly or in combination with other features and embodiments.

Figure 1:
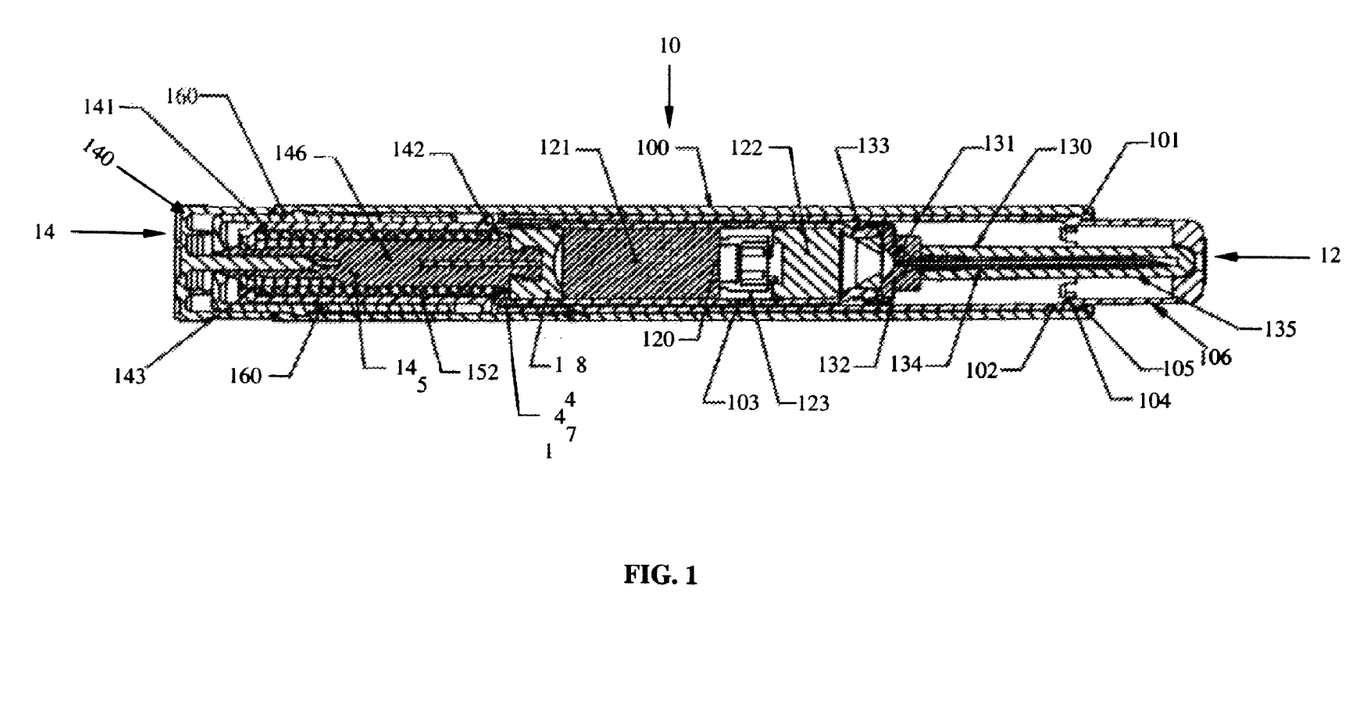
FIG. 1 is a longitudinal cross-sectional view of a wet/dry automatic injector according to the invention.

FIG. 1 shows a preferred embodiment of an automatic injector device that can be used in connection with the invention. Automatic injector device 10 has a needle end 12 and an activation end 14. The device has an outer body or housing assembly 100 having an in-turned shoulder 101. Located within the interior of housing assembly 100 are a cartridge holder body 102 and a cartridge assembly 103. Cartridge holder body 102 has a shoulder 104 that fits against seat 105 provided by in-turned shoulder 101. Cartridge holder body 102 also has a forward end portion 106 that is tapered to form a small circular aperture.

Cartridge assembly 103 within cartridge holder body 102 has an interior chamber 120 where the mixing of the therapeutic agent takes place. Chamber 120 is preferably a hollow cylinder with a smooth cylindrical inner surface. Chamber 120 has a first compartment 121 and a second compartment 122. Preferably, the liquid injection solution or liquid component is located within the first compartment 121 (referred to hereinafter as the "wet" compartment), and the therapeutic agent or dry component is located within the second compartment 122 (referred to hereinafter as the "dry" compartment).

A seal structure 123 annularly engages the interior side walls (i.e., the smooth cylindrical inner surface) of chamber 120 to seal the wet compartment from the dry compartment and to prevent seepage of the liquid injection solution into the dry compartment prior to activation of the injector device. Seal structure 123 has a sealed state and a flow-through state.

A needle assembly 130 mounts to the forward end of chamber 120 to inject the therapeutic agent upon activation of the injector device. In this embodiment, the forward end portion of chamber 120 has an annular groove 133 formed therein for attachment of needle assembly 130. Needle assembly 130 includes a funnel-shaped needle support 131 and has a crimp clamp 132 that is mechanically rolled into annular groove 133 to permanently secure and seal the needle assembly to chamber 120. Needle support 131 can be made of a resilient plastic material or metal with a rubber seal. Needle support 131 forms a sealed fluid channel from chamber 120 to needle 134. A rubber needle sheath 135 surrounds needle 134 and receives the narrow end of needle support 131. The overall length of cartridge assembly 103 is such that it is all contained within cartridge holder body 102, as shown in FIG. 1.

As also shown in FIG. 1, the outer body or housing assembly 100 has a length that accommodates cartridge holder body 102 and a stored energy assembly 140. The stored energy assembly can be any conventional type known in the art, such as the forward end activating device disclosed in U.S. Pat. No. 3,712,301, the disclosure of which is incorporated herein by reference. In another example, rather than employing a spring, the stored energy assembly may employ a charge of compressed gas or other suitable stored energy source.

As further shown in FIG. 1, stored energy assembly 140 has an inner sleeve 141 and an outer sleeve 160. Inner sleeve 141 has an out-turned flange 142 and an end wall 143. Out-turned flange 142 fits up against the end of cartridge holder body 102 when the stored energy assembly is inserted in housing assembly 100. Note that the length of outer sleeve 160 is slightly less than that of inner sleeve 141 to leave space between the wall of outer sleeve 160 and flange 142 of inner sleeve 141. A collet 145 fits within the out-turned flange end of inner sleeve 141. The collet has a body portion 146 and a head portion 147. The diameter of head portion 147 is larger than body portion 146 and is generally slightly smaller than that of a plunger 148. A coil spring 152 is positioned over collet body 146 and abuts head portion 147 at one end and the inner face of an end wall 143 of inner sleeve 141 at the other end.

Figure 2:
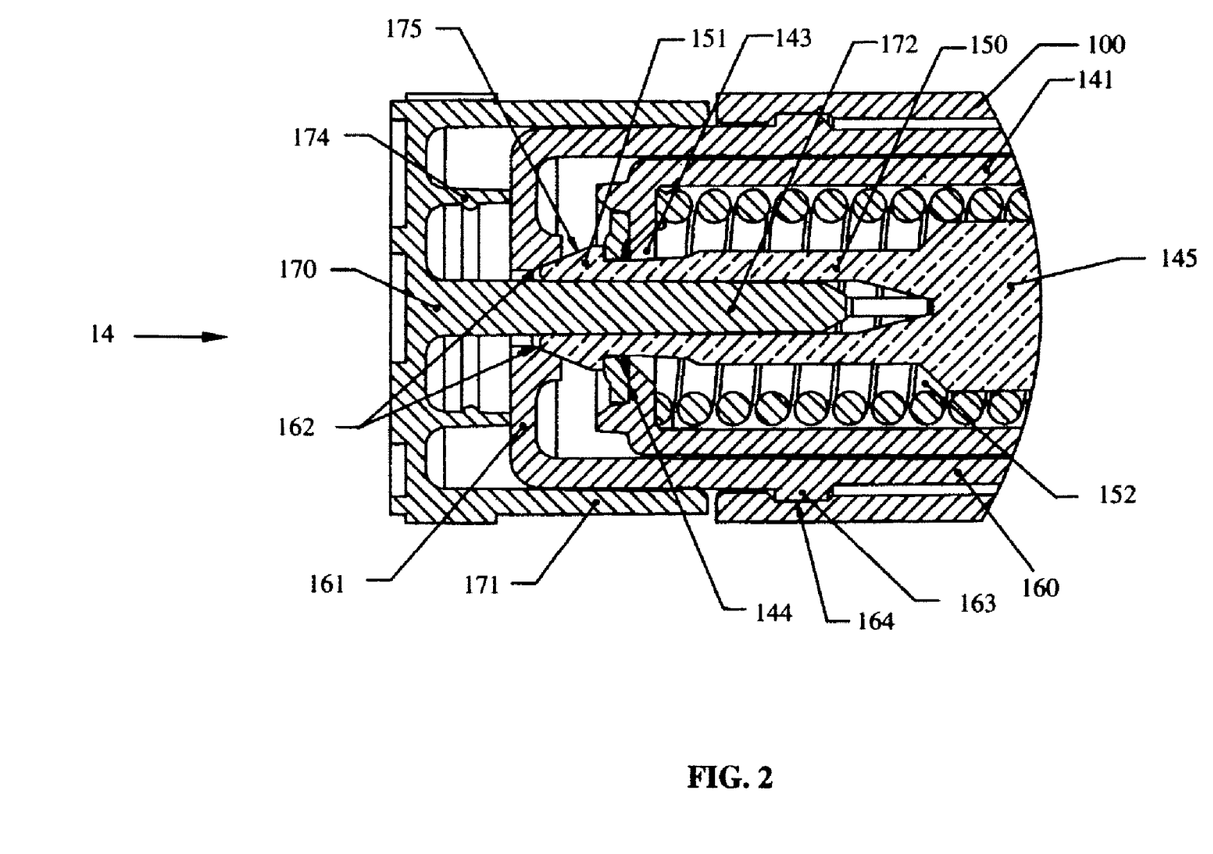
FIG. 2 is a longitudinal cross-sectional view of the activation end of the wet/dry automatic injector of FIG. 1.

FIG. 2 shows activation end 14 of the automatic injector of FIG. 1. Collet 145 has four equally-spaced, longitudinally extending spring fingers 150 terminating in frusto-conical locking detent heads 151. These locking detent heads maintain collet 145 and inner sleeve 141 in an assembled position with a coil spring 152 compressed there between. Upon compression of coil spring 152, detent heads 151 can be cammed inwardly by engaging the periphery of the opening of end wall 143. Detent head 151 can then be passed there through, whereupon the bases of detent heads 151 come to rest on retaining surface 144 of end wall 143 of inner sleeve 141 to retain collet 145 and inner sleeve 141 in the assembled condition with coil spring 152 compressed there between. When desired, the rear planar surface of the inner sleeve can be overlaid with a metal washer, in which case providing a guide and holding-flange to surround the opening is advantageous.

Outer sleeve 160 has a closed end 161 with a central aperture from which extends a frusto-conical surface 162. Surface 162 is sized and shaped to cooperate with frusto-conical detent heads 151 to cam the heads radially inward. Outer sleeve 160 is provided with a circumferential locking rib 163 that fits in an annular groove 164 in housing assembly 100 to retain the stored energy assembly in position in the housing assembly. As noted above, the length of outer sleeve 160 is slightly less than that of inner sleeve 141 to leave space between the inner wall of outer sleeve 160 and flange 142 of inner sleeve 141. This allows the two sleeves to move relative to each other to cam frusto-conical detent heads 151 inwardly during operation of the device.

To make certain that frusto-conical detent heads 151 are not accidentally cammed inward, a safety pin assembly 170 is provided. Safety pin assembly 170 has a cylindrical sleeve 171 sized to fit over the end portion of outer sleeve 160. A safety pin 172 extends inwardly from the center of safety pin assembly 170 into the opening formed by the inner portions of detent heads 151 to thereby prevent inward movement of the detent heads. Safety pin assembly 170 is provided internally with a plurality of spacer abutments 174 to assure proper positioning of the cap on outer sleeve 160.

To activate the injector, safety pin assembly 170 is manually pulled off the rear end of the injector, thus removing pin 172 from between fingers 150. Needle end 12 of injector 10 is positioned at the desired injection site. A telescoping action takes place between housing assembly 100 and cartridge holder body 102. This telescoping action causes the sleeves of the stored energy assembly to telescope. This causes frusto-conical surface 162 of outer sleeve 160 to engage the sloping surface 175 of detent heads 151 of spring fingers 150. This forces detent heads 151 inward toward one another and off of retaining surface 144 of end wall 143. Coil spring 152 is then free to release the stored energy therein to move collet 145 forwardly (i.e., toward needle end 12) under the force of coil spring 152 to effect an injection operation.

Figure 3:
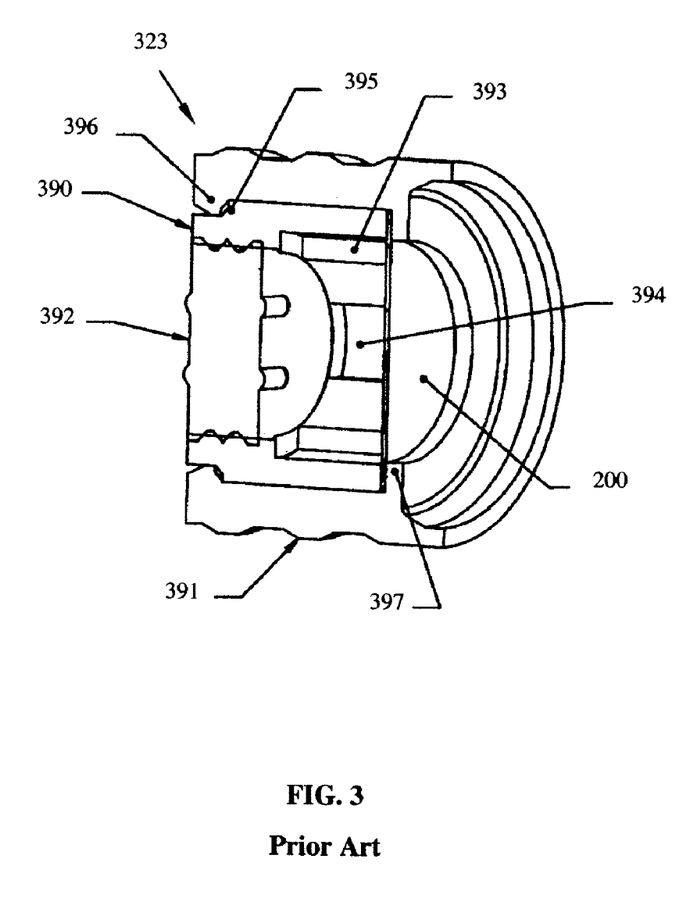
FIGS. 3 and 4 are perspective cross-sectional and perspective views, respectively, of a known seal structure with a laminar flow membrane.
Figure 4:
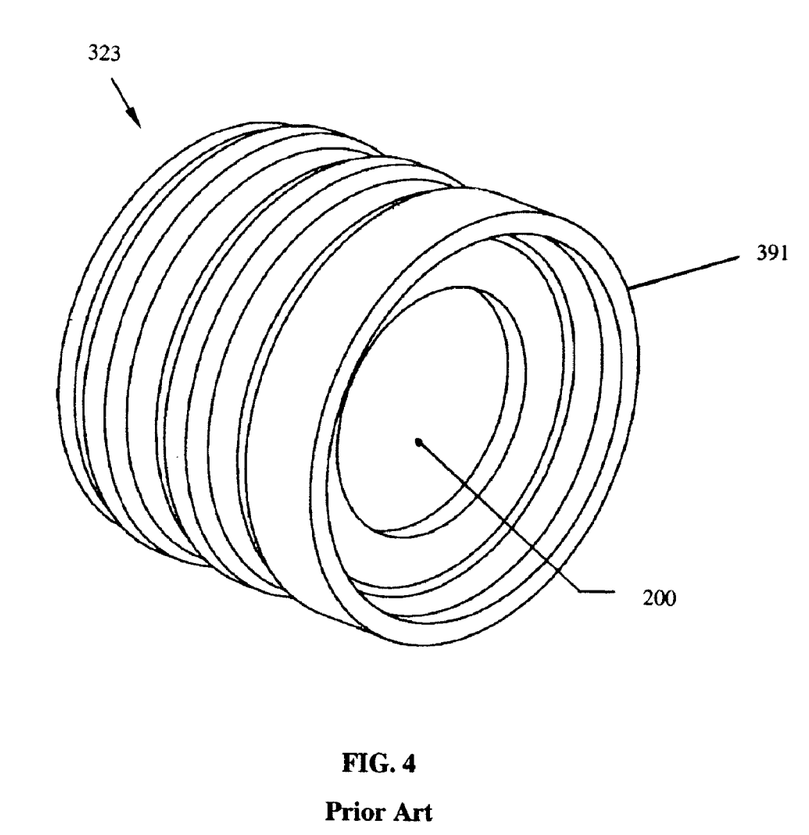

FIGS. 3 and 4 show a known seal structure 323 that has no fluid-directing member. Seal structure 323 can be used to separate a wet compartment from a dry compartment and has a sealed state and a flow-through state. Seal structure 323 has an internal rigid member 390, an outer seal 391, and a movable inner seal plug 392. Internal rigid member 390 has at least one by-pass channel 393 that creates at least one flow path, such that a liquid component in the wet compartment may be placed in fluid communication with the dry compartment. When plug 392 is moved forward (i.e., towards the needle) to by-pass area 394, the seal structure is placed in the flow-through state, which opens a flow path through by-pass channel 393. Internal rigid member 390 and outer seal 391 may optionally be secured together using any bonding techniques known in the art. Further, internal rigid member 390 and outer seal 391 may be formed such that they securingly engage each other using a combination of notched recesses 395 and extending shoulders 396 and 397. Optionally, seal structure 323 can include a laminar flow membrane or filter 200 which can be held in place between internal rigid member 390 and shoulder 397 of outer seal 391. Filter 200 can be made of any suitable medically-appropriate material that allows the therapeutic agent, when dissolved in the liquid component, to pass through while preventing any undissolved portions of the therapeutic agent or any impurities from passing through. The filter can be fabricated from metallic, ceramic, or polymeric materials, or a combination thereof. Suitable metallic materials include metals and alloys such as stainless steel.

Figure 5:
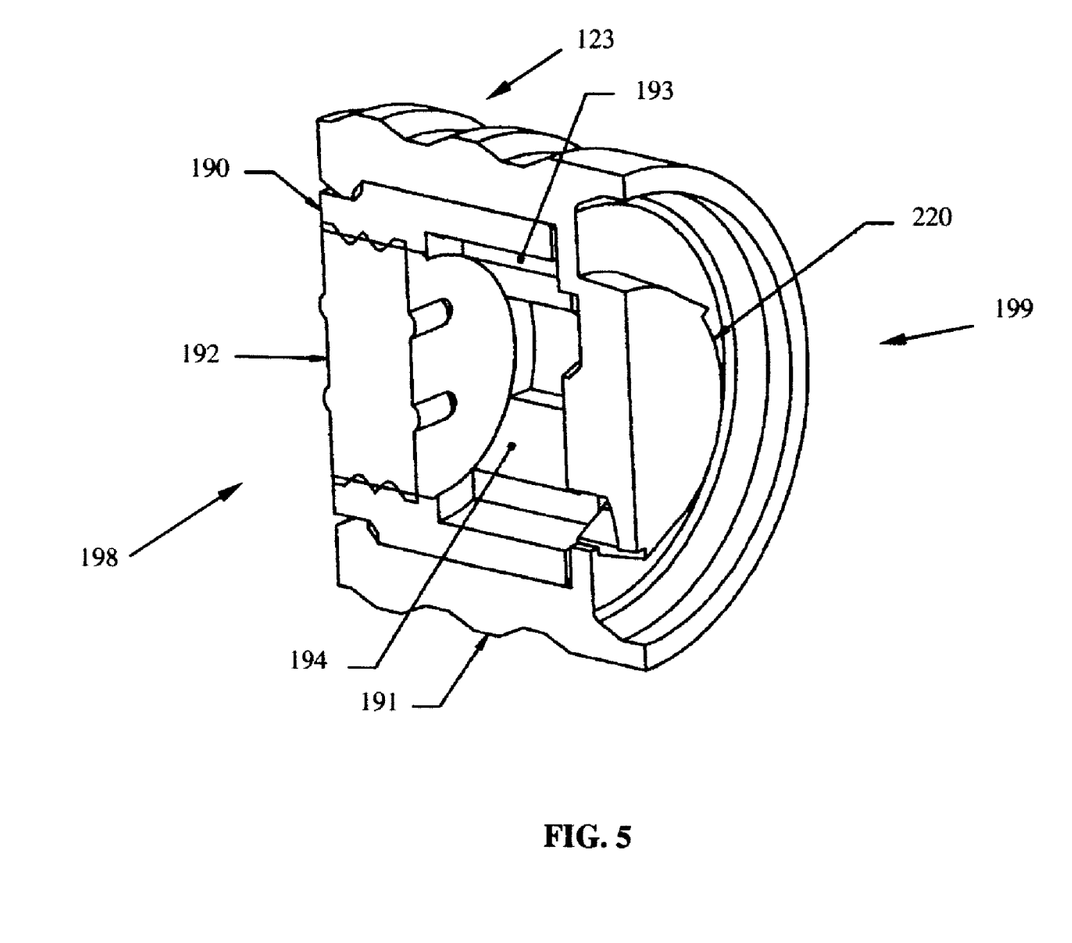
FIGS. 5 and 6 are perspective cross-sectional views of a seal structure with a fluid-directing member according to the invention.
Figure 6:
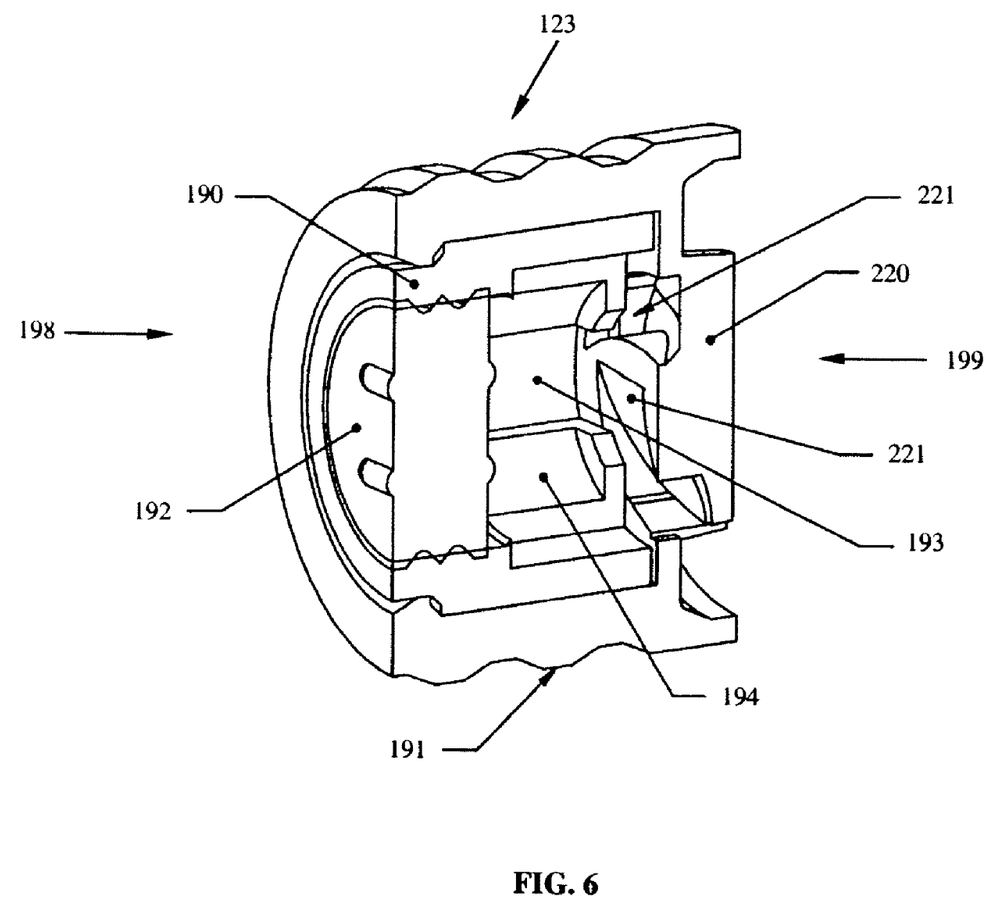

FIGS. 5 and 6 show seal structure 123 with a fluid-directing member 220 in accordance with the invention. Seal structure 123 has a sealed state and a flow-through state and preferably includes an internal rigid member 190, an outer seal 191, and a movable inner seal plug 192. Rigid member 190 and outer seal 191 may be constructed as described above for rigid member 390 and outer seal 391. Inner seal plug 192 is shown in FIGS. 5 and 6 in a first position, which places seal structure 123 in the sealed state. That is, seal structure 123 prevents liquid in the wet compartment from flowing through the seal structure to the dry compartment. Internal rigid member 190 has at least one by-pass channel 193. When plug 192 is moved from its first position to by-pass area 194 (i.e., a second position), a flow path is created via by-pass channel 193, and seal structure 123 is in the flow-through state.

Outer seal 191 has a first end 198 (towards the back, or activating end of the injector device) and a second end 199 (towards the front, or needle end of the device). Preferably, the first end is adjacent the wet compartment and the second end is adjacent the dry compartment. The fluid-directing member 220 is located at the second end. Optionally, the seal structure can include a filter or membrane 200 (as in seal structure 323) mounted between the flow path and fluid-directing member 220.

Fluid-directing member 220 has at least one channel 221 having a fluid exit port 222 into the dry compartment. Fluid exit port 222 has an opening that preferably fully faces the inner side surface of chamber 120 (see FIG. 8). More particularly, in one embodiment, the fluid port opening when viewed in a direction parallel to the central longitudinal axis 600 is parallel to the inner side surface of the chamber. Channel 221 is preferably shaped as a helix and is thus a helical channel. In other embodiments, the channels may be any shape that facilitates creation of a vortex by the liquid component as it enters the dry compartment. For example, the channels may be linear, circular, helical, inclined, or any combination thereof, provided a vortex is created. Multiple channels in the same fluid-directing member can each be a similar or identical shape or a different shape.

Figure 7:
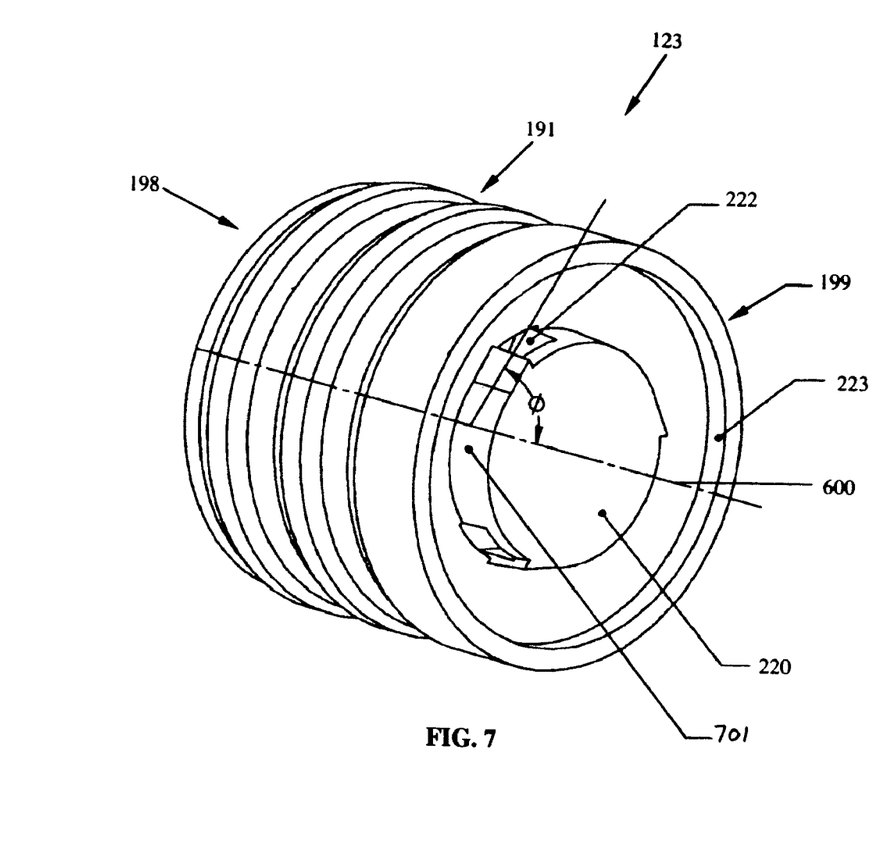
FIG. 7 is a perspective view of the seal structure of FIGS. 5 and 6.

FIG. 7 shows seal structure 123 with outer seal 191 and fluid-directing member 220. Fluid-directing member 220 has an annular surface 701 preferably parallel to the central longitudinal axis 600. The opening of each fluid exit port 222 is located on annular surface 701. Outer seal 191 may include an annular ridge 223 extending from second end 199. In preferred embodiments, the fluid exit port openings 222 fully face annular ridge 223. That is, the curved planes of the openings are parallel to the curvature of the annular ridge. The fluid-directing member 220 may extend axially beyond second end 199 by the same distance as ridge 223 and, alternatively, may extend axially beyond ridge 223. In those embodiments where the outer seal does not have a ridge, the fluid-directing member may be flush with second end 199 or, alternatively, may extend beyond the second end of the seal structure.

Figure 8:
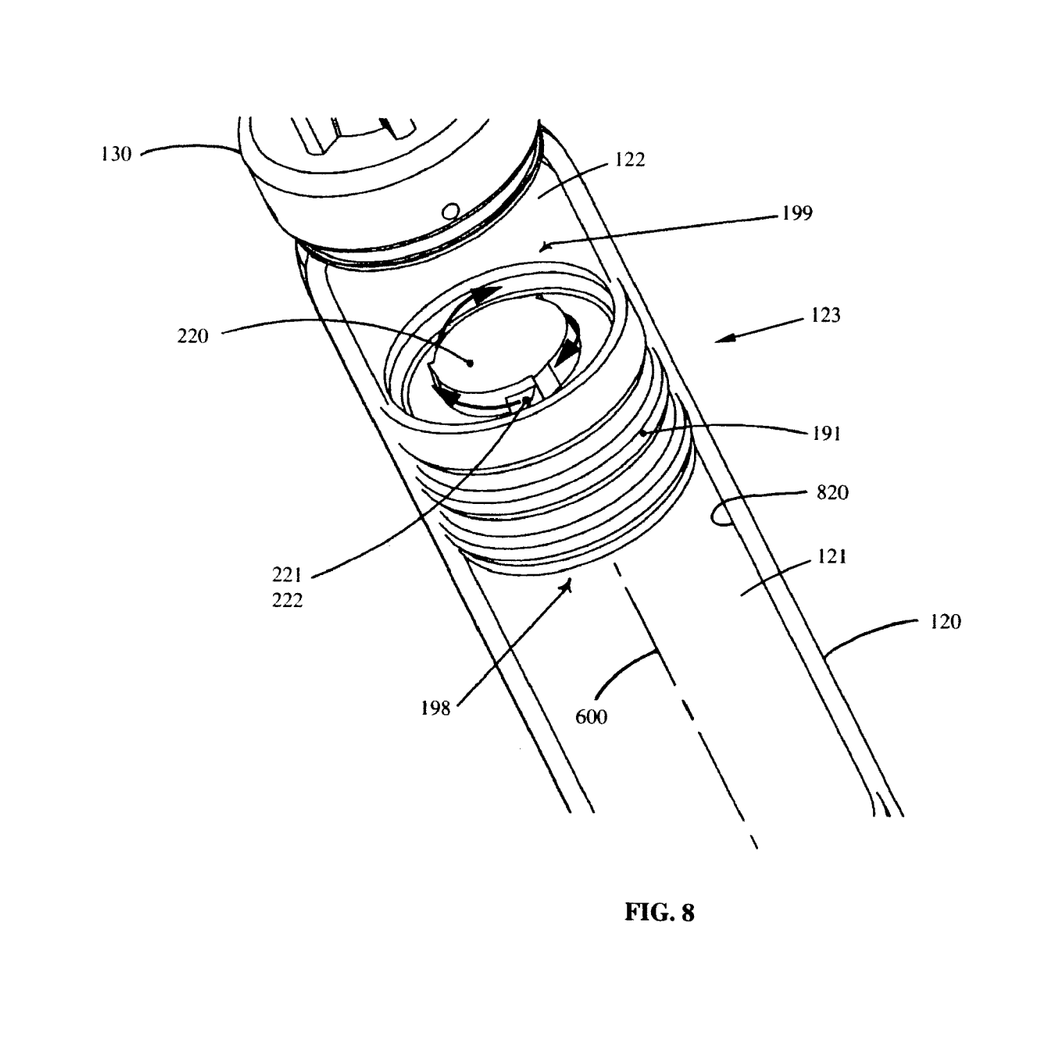
FIG. 8 is a perspective view of the seal structure of FIGS. 5-7 located within a chamber of an automatic injector according to the invention.
Figure 10:
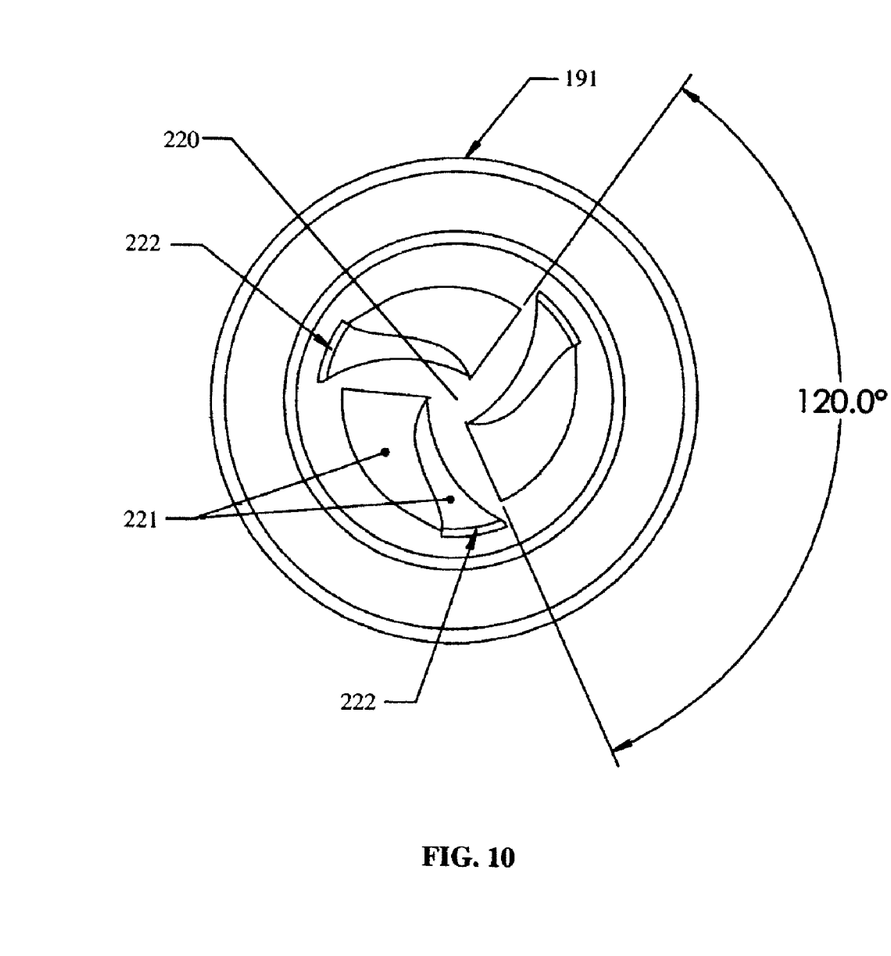
FIG. 10 is a rear elevational view of the inside of an outer seal with a fluid-directing member.

In the embodiment shown in FIG. 7, fluid-directing member 220 has three helical channels 221 and three fluid exit ports 222 (see also FIGS. 8 and 10). The fluid-directing member can have other numbers of channels. For example, the fluid-directing member can have one, two, three, four, or more channels. The channels can be separate or interconnected. Also, the channels can be oriented at various angles with respect to the longitudinal axis of the housing assembly. For example, the helical channels are preferably oriented at an angle Ø ranging from about 80° to 90° with respect to the longitudinal axis 600 of the housing assembly. Optionally, they can alternatively be oriented at an angle Ø ranging from about 10° to 90°. Also, multiple channels can each be oriented at a different angle or, alternatively, can each be oriented at the same angle.

FIG. 8 shows a seal structure 123 with outer seal 191 and fluid-directing member 220 in an automatic injector chamber 120. Outer seal 191 sealingly engages the inner side surface 820 of chamber 120 to prevent passage of liquid from wet compartment 121 to dry compartment 122 between the outer seal 191 and the inner side surface 820. Preferably, first end 198 of outer seal 191 is adjacent wet compartment 121, and second end 199 of outer seal 191 is adjacent dry compartment 122. Second end 199 has fluid-directing member 220 thereon, which has three helical channels 221 and three corresponding fluid exit port openings 222. Once by-pass channels 193 are open, liquid from the wet compartment can flow through the channels and into the fluid-directing member. The helical channels and fluid exit ports in the fluid-directing member cause the liquid entering the dry compartment to move in a circular motion, creating a vortex. The configuration of helical channels 221, combined with the location of the fluid exit ports 222 radially around center longitudinal axis 600 and between the center longitudinal axis and the inner side surface of the chamber advantageously provides the liquid entering the dry compartment with flow components in axial, circumferential, and radial directions. Note that the openings of the fluid exit ports of the invention do not face directly forward toward needle assembly 130. Preferably, most, if not all, of the liquid entering the dry compartment enter at an angle of about 80° to 90° with respect to longitudinal axis 600 of the outer body/housing assembly. This geometry causes the liquid to have a substantial circumferential flow component that facilitates formation of a vortex. The formation of a vortex effectively mixes the wet and dry components of the auto-injector when the device is activated, thus dispensing increased amounts of the (originally) dry therapeutic agent, as compared to a comparable device without the fluid-directing member. The vortex improves mixing of the liquid with the therapeutic agent, and thus improves dissolution of the therapeutic agent.

Figure 9:
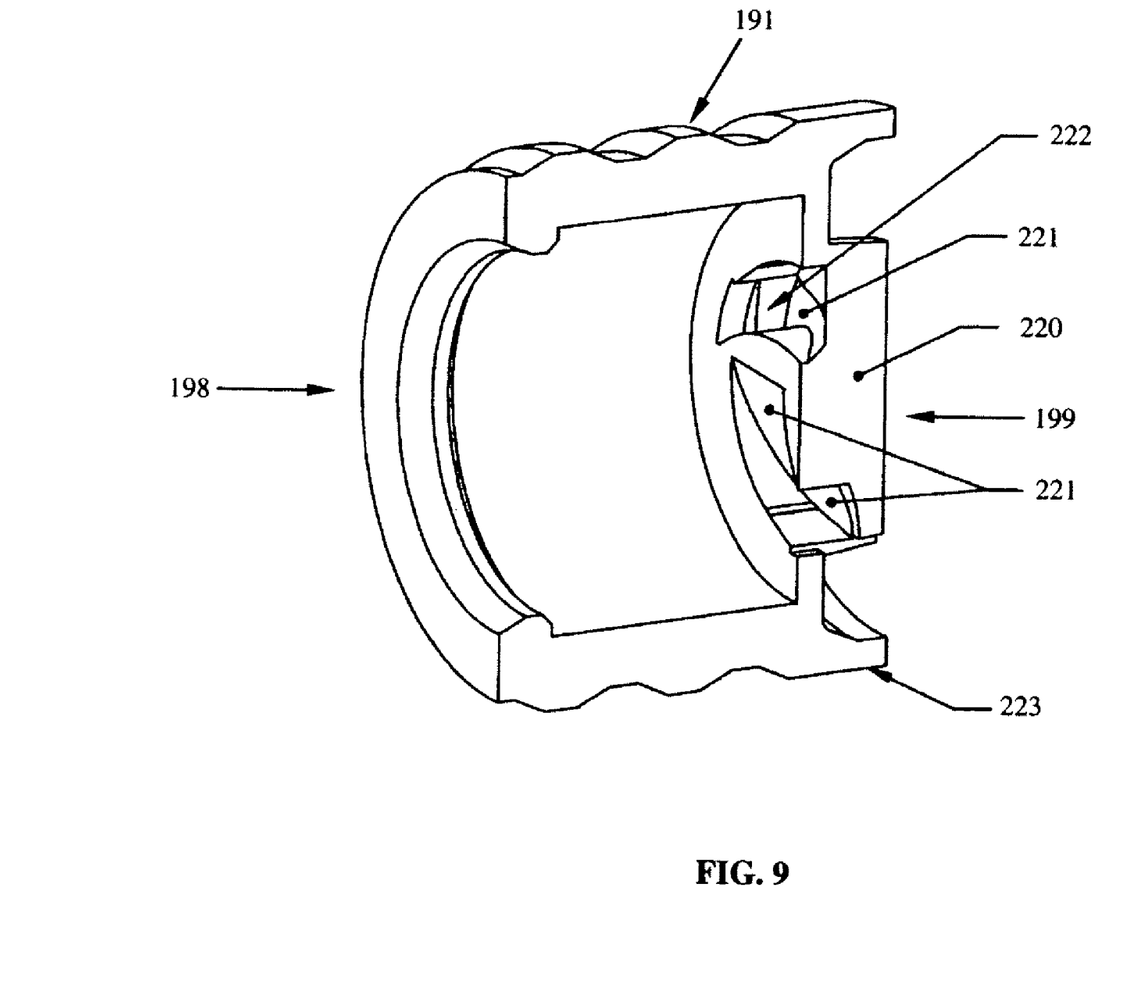
FIG. 9 is a perspective cross-sectional view of an outer seal integrally formed with a fluid-directing member according to the invention.

The outer seal and the fluid-directing member may be integrated into a single unit; that is, they may be manufactured as one piece, as shown in FIG. 9.

FIG. 10 shows the inside of outer seal 191 with a fluid directing member 220. In this embodiment, fluid-directing member 220 has three helical channels 221 each with a respective fluid exit port 222. Each channel preferably has at least one exit port. Fluid exit ports 222 are offset from each other by preferably about 120° (i.e., the three exits ports are arranged radially equidistantly around the central longitudinal axis). Preferably, embodiments with multiple fluid exit ports 222 have the exit ports arranged radially equidistantly around the central longitudinal axis.

The invention is also directed to methods of assembling an automatic injector for administrating a liquid solution and to methods of preparing a liquid solution in an automatic injector. In one embodiment, a method includes providing a chamber and placing a seal structure in the chamber to create two compartments, a wet compartment suitable for containing a liquid component and a dry compartment suitable for containing a dry component. The seal structure has a first state that seals the liquid component in the wet compartment and at least one flow path that is closed when the seal structure is in the first state. The seal structure also has a second state, wherein the flow path is open to allow the liquid component to flow through the seal structure. The seal structure includes an outer seal that has an end adjacent the wet compartment and an end adjacent the dry compartment. The end adjacent the dry compartment has at least one helical channel capable of allowing the liquid component to flow into the dry compartment when the seal structure is in the second state. The method also includes loading a liquid in the wet compartment, loading a dry substance in the dry compartment, and attaching a needle assembly to the dry compartment of the chamber. The method further includes affixing a helical channel between the two compartments such that the liquid enters the second compartment circumferentially at an angle of preferably about 80° to 90° with respect to a longitudinal axis of the chamber. This facilitates formation of a liquid vortex in the dry compartment to improve and accelerate the mixing and dissolution of the dry substance with the liquid.

EXAMPLES

The results shown in Tables 1 and 2 below demonstrate the improved mixing and dissolution capabilities of the fluid-directing member of the invention.

Table 1 shows test results of administering a dry component mixed with a liquid component using an auto-injector with a fluid-directing member. Table 2 shows test results of administering a dry component mixed with a liquid component using an auto-injector without a fluid-directing member.

The tests were done by first loading a sample of a dry component into a wet/dry auto-injector. The auto-injector was then activated, allowing the liquid component to mix with the dry component before being dispensed. The dispensed sample was collected in a container and the dispensed sample and container were weighed. The liquid component was then removed and the dry component and container were weighed. The dispensed solid mass was determined. Also, the mixing/dispensing time was measured.

TABLE 1

Devices with Fluid-Directing Member

| Loaded | | Dispensed | | Operational | |
| --- | --- | --- | --- | --- | --- |
| Dry Powder mg | Fluid mL | Dry Powder % | mg | Fluid mL | Time sec |
| 687 | 2.199 | 96.8 | 665 | 1.837 | 3.102 |
| 687 | 2.206 | 96.7 | 664 | 1.844 | 2.393 |
| 688 | 2.204 | 95.1 | 654 | 1.808 | 2.900 |
| 687 | 2.203 | 96.2 | 661 | 1.830 | 2.798 |

Average is last number in each column, indicated in bold

TABLE 2

Device without Fluid-Directing Member

| Loaded | | Dispensed | | Operational | |
| --- | --- | --- | --- | --- | --- |
| Dry Powder mg | Fluid mL | Dry Powder % | Mg | Fluid mL | Time sec |
| 690 | 2.207 | 85.9 | 593 | 1.806 | 3.072 |
| 696 | 2.211 | 87.2 | 607 | 1.595 | 3.244 |
| 687 | 2.203 | 97.2 | 668 | 1.788 | 3.469 |
| 691 | 2.207 | 90.1 | 623 | 1.730 | 3.262 |

Average is last number in each column, indicated in bold

The results show that the auto-injector with a fluid-directing member constructed in accordance with the invention dissolved and dispensed, on average, a greater amount of the dry component more quickly.

The greater amounts of dry component being dissolved, as well as, the faster dispensing time are attributed to the fluid-directing member. As the liquid component passes through the fluid-directing member, a vortex is created that helps the liquid quickly dissolve the dry component, and because the dry component obstructs the liquid component's path to the needle, the quicker the dry component is dissolved, the faster the liquid can pass through the needle.

The invention has thus been described in connection with the preferred embodiments. The invention is not, however, limited to these embodiments, which are only examples of the invention. Persons skilled in the art will appreciate that various changes and modifications can be made within the scope of the invention, which is limited only by the claims which follow.

All references cited above are incorporated herein, in their entirety, for all purposes related to this disclosure.

We claim:

1. An automatic injector comprising:
a housing assembly having a central longitudinal axis;
an interior chamber located within the housing assembly, the interior chamber having an inner side surface extending in the direction of the longitudinal axis, and
a seal structure positioned in the interior chamber to form a dry compartment and a wet compartment, the dry compartment suitable for containing a dry substance and the wet compartment suitable for containing a liquid, the seal structure positioned between the dry compartment and the wet compartment, the seal structure comprising:
a first end adjacent the wet compartment;
a second end adjacent the dry compartment;
an outer seal that sealingly engages the inner side surface of the interior chamber to prevent passage of liquid between the outer seal and the inner surface of the chamber, and
a fluid-directing member located on the second end of the seal structure, the fluid-directing member comprising a channel having a fluid exit port into the dry compartment, the fluid exit port having an opening that fully faces the inner side surface of the chamber.

2. The automatic injector of claim 1, wherein the fluid-directing member is located radially inward from the outer seal on the second end of the seal structure.

3. The automatic injector of claim 1, wherein the outer seal has an annular ridge around the second end and the fluid exit port opening fully faces the annular ridge.

4. The automatic injector of claim 1, wherein the fluid-directing member has a annular surface parallel to the central longitudinal axis and the fluid exit port opening is located on the annular surface.

5. The automatic injector of claim 1, wherein the channel is oriented at an angle of between about 80° to 90° with respect to the central longitudinal axis of the housing assembly.

6. The automatic injector of claim 1, wherein the channel is helical about the central longitudinal axis.

7. The automatic injector of claim 1, wherein the fluid-directing member comprises a plurality of channels.

8. The automatic injector of claim 7, wherein the channels are interconnected.

9. The automatic injector of claim 7, wherein the channels are separate.

10. The automatic injector of claim 1, wherein the channel is helical, circular, or a combination thereof.

11. The automatic injector of claim 1, wherein the channel is configured to provide fluid passing through the seal structure with a substantial circumferential flow component.

12. The automatic injector of claim 1, wherein the outer seal and the fluid-directing member form a single integrated unit.

13. The automatic injector of claim 1, wherein the fluid-directing member extends axially beyond the outer seal.

14. An automatic injector comprising:
a housing assembly having a central longitudinal axis;
an interior chamber located within the housing assembly, the interior chamber having an inner side surface extending in the direction of the longitudinal axis;
a needle assembly located within the housing assembly and in communication with the interior chamber to dispense a liquid solution from the interior chamber; and
a seal structure positioned in the interior chamber to form a dry compartment and a wet compartment, the dry compartment suitable for containing a dry substance and the wet compartment suitable for containing a liquid, the seal structure positioned between the dry compartment and the wet compartment, the seal structure comprising:
an outer seal that sealingly engages the inner side surface of the interior chamber to prevent liquid from passing between the outer seal and the inner surface of the chamber,
a rigid member in communication with the outer seal,
a flow path through the seal structure,
a fluid-directing member in communication with the rigid member and the flow path and adjacent the dry compartment, the fluid-directing member comprising a helical channel; and
an inner seal plug in communication with the rigid member having a first position with respect to the rigid member that closes the flow path to prevent passage of liquid through the flow path, the inner seal plug having a second position with respect to the rigid member that opens the flow path and allows a liquid in the wet compartment to flow through the flow path and the helical channel into the dry compartment.

15. The automatic injector of claim 14, wherein the helical channel has a fluid exit port, the fluid exit port having an opening that fully faces the inner side surface of the chamber.

16. The automatic injector of claim 14, wherein the outer seal and the rigid member form a single integrated unit.

17. The automatic injector of claim 14, wherein the outer seal attaches to the rigid member.

18. The automatic injector of claim 14, wherein the rigid member is formed from at least two rigid member parts that are welded or bonded together.

19. The automatic injector of claim 14, wherein the fluid-directing member and the rigid member form a single integrated unit.

20. The automatic injector of claim 14, wherein the fluid-directing member attaches to the rigid member.

21. An automatic injector comprising:
a housing assembly having a central longitudinal axis;
an interior chamber located within the housing assembly, the interior chamber having an inner side surface extending in the direction of the longitudinal axis;
a needle assembly located within the housing assembly and in communication with the interior chamber to dispense a liquid solution from the interior chamber; and
a seal structure positioned in the interior chamber to form a dry compartment and a wet compartment, the dry compartment suitable for containing a therapeutic agent and the wet compartment suitable for containing a liquid, the seal structure positioned between the dry compartment and the wet compartment and forming an annular seal between an outer surface of the seal structure and the inner side surface of the interior chamber, the annular seal preventing liquid from passing between the outer surface of the seal structure and the inner surface of the chamber, the seal structure having a sealed state and a flow-through state, the sealed state preventing liquid from passing through the seal structure and the flow-through state allowing liquid to pass through the seal structure, the seal structure comprising:
at least one channel within the seal structure at an end of the seal structure adjacent the dry compartment, the at least one channel in fluid communication with a by-pass channel in the seal structure and having a plurality of exit ports that open into the dry compartment, each of the exit ports arranged circumferentially around the central longitudinal axis, each of the exit ports having an opening oriented at an angle of between about 80° to 90° with respect to the central longitudinal axis.

22. The automatic injector of claim 21, wherein the seal structure comprises a plurality of channels corresponding respectively to the plurality of exit ports.

23. The automatic injector of claim 22, wherein the plurality of channels are each separate, each channel having a respective one of the plurality of exit ports.

24. The automatic injector of claim 21, wherein the channel is helical with respect to the central longitudinal axis.

25. The automatic injector of claim 21, wherein the channel causes fluid passing through the seal structure to form a vortex in the dry compartment.

26. The automatic injector of claim 21, wherein the channel provides fluid passing through the seal structure with a substantial circumferential flow component.

27. The automatic injector of claim 21, wherein the plurality of exit ports are arranged equidistantly around the central longitudinal axis.

28. The automatic injector of claim 21, wherein the plurality of exit ports are three exit ports spaced about 120 degrees apart around the central longitudinal axis.

29. A method of assembling an automatic injector for administration of a liquid solution, the method comprising:
providing a housing having a hollow interior;
providing a chamber having first and second ends and a longitudinal axis;
attaching a plunger to the first end of the chamber;
loading a liquid in the chamber;
inserting a seal structure in the chamber to create first and second compartments, the seal structure having a sealed state and a flow-through state, the liquid located in the first compartment, the seal structure having a helical channel adjacent the second compartment, the helical channel configured to allow a liquid to pass there through from the first compartment to the second compartment such that the liquid enters the second compartment circumferentially at an angle of about 80° to 90° with respect to the longitudinal axis of the chamber when the seal structure is in the flow-through state;
loading a dry substance in the second compartment;
attaching a needle assembly to the second end of the chamber; and
placing the chamber, needle assembly, and plunger in the housing.

30. The method of claim 29, wherein loading a liquid and attaching a plunger occurs after attaching a needle assembly, loading a dry substance, and inserting a seal structure.

31. The method of claim 29, wherein inserting a seal structure occurs before attaching a plunger and loading a liquid and after attaching a needle assembly and loading a dry substance.

32. A method of preparing a liquid solution in an automatic injector, the liquid solution comprising a liquid and a dry substance, the method comprising:
loading a liquid in a first compartment of a chamber, the chamber having a longitudinal axis;
loading a dry substance in a second compartment of the chamber, the first and second compartments separated from each other by a seal structure having a sealed state and a flow-through state, the seal structure initially in the sealed state, the sealed state sealing the first compartment from the second compartment to prevent the liquid from flowing into the second compartment;

converting the seal structure from the sealed state to the flow-through state to allow the liquid to flow from the first compartment into the second compartment; and forcing the liquid to flow into the second compartment in the form of a vortex to mix with the dry substance.

33. The method of claim 32, wherein loading a dry substance occurs before loading a liquid.

34. The method of claim 32, wherein forcing the liquid further comprises forcing the liquid to flow into the second compartment circumferentially at an angle of about 80° to 90° with respect to the longitudinal axis of the chamber.

35. The method of claim 32, wherein forcing the liquid further comprises forcing the liquid to flow through a helical channel into the second compartment to form a vortex in the second compartment.

* * * * *